US011518956B2

(12) United States Patent
Hedoire et al.

(10) Patent No.: US 11,518,956 B2
(45) Date of Patent: Dec. 6, 2022

(54) ALKOXYLATED PHOSPHATE ESTERS FOR LUBRICANT COMPOSITIONS

(71) Applicant: RHODIA OPERATIONS, Paris (FR)

(72) Inventors: Claude-Emmanuel Hedoire, Ezanville (FR); Ramona Gironda, Ospiate di Bollate (IT)

(73) Assignee: RHODIA OPERATIONS, Paris (FR)

( * ) Notice: Subject to any disclaimer, the term of this patent is extended or adjusted under 35 U.S.C. 154(b) by 76 days.

(21) Appl. No.: 16/061,128

(22) PCT Filed: Dec. 13, 2016

(86) PCT No.: PCT/EP2016/080795
§ 371 (c)(1),
(2) Date: Jun. 11, 2018

(87) PCT Pub. No.: WO2017/102726
PCT Pub. Date: Jun. 22, 2017

(65) Prior Publication Data
US 2018/0371354 A1    Dec. 27, 2018

(30) Foreign Application Priority Data

Dec. 14, 2015   (FR) ...................................... 1562264

(51) Int. Cl.
| | | |
|---|---|---|
| *C10M 153/04* | (2006.01) | |
| *C10M 173/00* | (2006.01) | |
| *C10M 137/04* | (2006.01) | |
| *C10N 30/06* | (2006.01) | |
| *C10N 30/12* | (2006.01) | |
| *C10N 30/00* | (2006.01) | |
| *C10N 40/22* | (2006.01) | |
| *C10N 40/20* | (2006.01) | |
| *C07C 29/141* | (2006.01) | |

(52) U.S. Cl.
CPC ........ *C10M 153/04* (2013.01); *C10M 137/04* (2013.01); *C10M 173/00* (2013.01); *C07C 29/141* (2013.01); *C10M 2203/106* (2013.01); *C10M 2215/042* (2013.01); *C10M 2223/02* (2013.01); *C10M 2225/00* (2013.01); *C10N 2030/06* (2013.01); *C10N 2030/12* (2013.01); *C10N 2030/24* (2020.05); *C10N 2040/22* (2013.01); *C10N 2040/245* (2020.05)

(58) Field of Classification Search
CPC .................................................. C10M 2223/02
USPC ........................................................ 558/186
See application file for complete search history.

(56) References Cited

U.S. PATENT DOCUMENTS

| | | | |
|---|---|---|---|
| 3,933,658 A | 1/1976 | Beiswanger et al. | |
| 4,351,738 A * | 9/1982 | Takahashi ............... | D06M 7/00 428/395 |
| 4,613,445 A | 9/1986 | Haack et al. | |
| 6,024,788 A * | 2/2000 | Tomioka ................ | C08K 5/521 106/281.1 |
| 6,548,557 B1 * | 4/2003 | Fogel ..................... | C09K 23/00 514/939 |
| 2004/0186309 A1 | 9/2004 | Matsunaga et al. | |

FOREIGN PATENT DOCUMENTS

| | | |
|---|---|---|
| CN | 104710610 A | 6/2015 |
| DE | 2756747 A1 | 6/1979 |
| JP | 2000212583 A | 8/2000 |
| JP | 2004217631 A | 8/2004 |
| JP | 2006045391 * | 2/2006 |
| WO | 0188070 A1 | 11/2001 |

OTHER PUBLICATIONS

Machine translation of JP2006045391, Feb. 16, 2006.*
Office Action issued in Chinese Application No. 201680081467.0, dated Dec. 18, 2020 (19 pages).
Office Action issued in Japanese Application No. 2018-530777, dated Sep. 23, 2020 (6 pages).

* cited by examiner

*Primary Examiner* — Ana Z Muresan
(74) *Attorney, Agent, or Firm* — Osha Bergman Watanabe & Burton LLP

(57) ABSTRACT

The present invention concerns a composition suitable for working and shaping metals, in particular providing a lubricating effect, including polymers of the following formula: $[R\text{—}O(\text{—}CH(CH_3)\text{—}CH_2O\text{—})_n(CH_2\text{—}CH_2O\text{—})_p\text{—}]_{1+x}P(\text{=}O)(OH)_{2-x}$ in which: R is a linear or branched, preferably linear, saturated or unsaturated hydrocarbon group, comprising between 8 and 12 carbon atoms; n is a number, which may or may not be an integer, between 6 and 20; p is a number, which may or may not be an integer, between 4 and 25; and x is a number between 0 and 1, and in particular between 0.1 and 0.9.

16 Claims, No Drawings

ALKOXYLATED PHOSPHATE ESTERS FOR LUBRICANT COMPOSITIONS

This application is a U.S. national phase entry under 35 U.S.C. § 371 of International Application No. PCT/EP2016/080795, filed on Dec. 13, 2016, which claims priority to French Application No. 1562264, filed on Dec. 14, 2015. The entire contents of these applications are explicitly incorporated herein by this reference.

The present invention relates to additives for lubricating compositions intended for shaping and working metals, and more particularly the compositions used during metal cutting operations, which are typically in the form of emulsions, typically of naphthenic or paraffinic oils, in water. The invention relates more specifically to emulsifiers capable of providing, inter alia, an additional lubricating effect.

Emulsifiers that provide a lubricating effect of this type are already known, especially for metal-working applications, in particular for cutting metals. Amongst others, the use has been proposed within this context of a phosphate ester emulsifier which has the advantage of providing advantageous effects in addition to their emulsifying nature, and especially a lubricating effect. This lubricating effect, which is more or less pronounced depending on the precise nature of the phosphate ester, appears to be at least partly explained by an adsorption of the phosphorus-containing groups on the surface of the metals, whereby the phosphate esters form, schematically, a sort of protective wear-resistant layer on the surface of the metals. Phosphate esters further provide, for the most part, a specific protective effect for aluminum, for which they prevent the corrosion blackening ("staining"). Furthermore, phosphate esters are for the most part biodegradable.

That being so, outside of the aforementioned advantages, emulsifiers with a lubricating nature known up to this time have drawbacks. In particular, they result for the most part in a significant formation of foam, which limits or even prohibits their use in certain applications. Furthermore, they tend to precipitate, forming soaps, when they are used in hard water. Moreover, certain phosphate esters are ecotoxic. To date, no effective emulsifier has been described that does not exhibit one of these drawbacks. The Lubrhophos® LB400 emulsifier, for example, available from the company Solvay, provides a pronounced (wear-resistant) lubricating effect, but it forms soaps in hard water. Emulsifiers that have a reduced tendency to form soaps have been described, such as Lubrhophos® RD510E for example, but they generally have mediocre lubricating properties.

One objective of the present invention is to provide emulsifiers having a lubricating nature that can be used in metal-working compositions which have a good (wear-resistant) lubricating effect and which do not exhibit the aforementioned drawbacks.

For this purpose, the present invention provides specific alkoylated phosphate esters, for which the inventors have now demonstrated that, unexpectedly, they have very good lubricating properties together with a low tendency to form foam, a very reduced formation of soap in hard water and in addition a low ecotoxicity.

According to a first aspect, the present invention relates to these particular alkoylated phosphate esters. More specifically, one subject of the invention is a polymer composition including polymers corresponding to the formula (I) below:

$$[R-O(-CH(CH_3)-CH_2O-)_n(CH_2-CH_2O-)_p-]_{1+x}P(=O)(OH)_{2-x} \quad (I)$$

where:
R is a linear or branched, and preferably linear, saturated or unsaturated hydrocarbon-based group comprising from 8 to 12 carbon atoms
n is a number, integer or not, between 6 and 20
p is a number, integer or not, between 4 and 25
x is a number between 0 and 1, in particular between 0.1 and 0.9.

The formula (I) represents the number-average composition of the population of polymers.

The polymers present in this composition in general comprise a mixture of monoesters of formula:

$$R-O(-CH(CH_3)-CH_2O-)_n(CH_2-CH_2O-)_p-P(=O)(OH)_2$$

and of diesters of formula:

$$[R-O(-CH(CH_3)-CH_2O-)_n(CH_2-CH_2O-)_p-]_2P(=O)OH$$

x reflects the molar ratio between diesters and monoesters (x=0 corresponds to the case where the composition comprises only monoesters; x=1 corresponds to the case where the composition comprises only diesters).

The population of polymers may comprise several types of polymers comprising different R groups.

In the formula (I), the R group is preferably a saturated or monounsaturated alkyl group. It is advantageously a linear alkyl. The R group is a C8 to C12 group, namely it contains at least 8 and at most 12 carbon atoms. Advantageously, it is a C11 to C12 group. According to one particularly advantageous embodiment, the R group contains exactly 12 carbon atoms (C12 group).

One R group particularly suitable for the invention is the lauryl group (linear and saturated C12 alkyl). The polymers of the invention then correspond to the following formula (Ia):

$$[CH_3-(CH_2)_{11}-O-(CH(CH_3)-CH_2O-)_n(-CH_2-CH_2O-)_p]_{1+x}-P(=O)(OH)_{2-x} \quad (Ia)$$

where n, p and x have the aforementioned meanings, x in general being between 0.1 and 0.9.

In practice, the polymers of formula (Ia) are obtained starting from a mixture of alcohols of the lauryl cut and they may therefore be present in the composition of the invention as a mixture with other polymers that typically contain R groups of C8 to C16 alkyl type.

The aforementioned compounds of formulae (I) and (Ia) comprise, in this order, between the R group and the $-P(=O)(OH)_2$ group, firstly a sequence of propylene oxide units then a sequence of ethylene oxide units.

In the above formulae, n represents the number of propylene oxide units when referring to an isolated compound (in which case n is inevitably an integer) or else, most often, the average number of propylene oxide units in the case of a population comprising a mixture of compounds (in which case n may be an integer or a decimal number). Similarly, p represents the number of ethylene oxide units when referring to an isolated compound (in which case p is inevitably an integer) or else, most often, the average number of ethylene oxide units in the case of a population comprising a mixture of compounds (in which case p may be an integer or a decimal number).

In the compounds of the invention, n is less than or equal to 20 and in general remains less than or equal to 15, and typically less than or equal to 10. Furthermore, n is greater than or equal to 6, and more preferentially greater than or equal to 6.5, for example between 7 and 10.

Furthermore, in the compounds of the invention, p is less than or equal to 25 and in general remains less than or equal to 20, and typically less than or equal to 15. Furthermore, p is greater than or equal to 4, and more preferentially greater than or equal to 4.5, for example between 4.5 and 10.

According to one advantageous embodiment, n is equal to 7.5 and p is equal to 5.

One particularly useful compound according to the invention corresponds to the following formula (Ib):

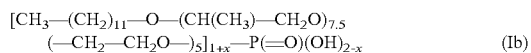
$$[CH_3-(CH_2)_{11}-O-(CH(CH_3)-CH_2O)_{7.5}(-CH_2-CH_2O-)_5]_{1+x}-P(=O)(OH)_{2-x} \quad (Ib)$$

where x has the aforementioned meaning, x in general being between 0.1 and 0.9.

These polymers of formula (Ib), which are a particular case of the aforementioned polymers (Ia) are themselves also typically obtained starting from a mixture of alcohols of the lauryl cut and may therefore be present in the composition of the invention as a mixture with other polymers that typically contain R groups of C8 to C16 alkyl type.

The polymers of the invention may be easily synthesized. Typically by propoxylation of an alcohol ROH (or of a mixture of alcohols) where R is the group present in the compound to be synthesized, whereby a compound RO—$(CH(CH_3)-CH_2O)_nH$ is formed that is then ethoxylated to form a compound RO—$(CH(CH_3)-CH_2O)_n(CH_2-CH_2O)_pH$ which may be converted into the phosphate ester of formula (I) by any means known per se, for example by reaction with $P_2O_5$, especially under the conditions of step 2 of example 1 below.

According to another aspect, the invention relates to the use of compositions including polymers corresponding to one of the aforementioned formulae (I), (Ia) or (Ib) in a lubricating formulation for working or shaping metals, preferably a lubricating emulsion, said composition typically being a lubricating composition for cutting metals, in particular aluminum.

The compositions of the invention provide, within this context, a lubricating effect, by schematically forming a wear-resistant protective layer on the surface of the metals. On aluminum, they additionally inhibit the blackening (coloration) by oxidation ("staining").

Furthermore, the compositions of the invention have emulsifying properties and they are therefore suitable for stabilizing an emulsion. They may therefore be used both for stabilizing a lubricating emulsion and for improving the emulsifying qualities of said emulsion. Typically, to form an emulsion of this type, the compositions of the invention may be incorporated into an oil (typically in a proportion of from 5% to 30%, for example between 10% and 25%, in particular around 20%, relative to the compound+oil total mass), then this mixture is mixed with water (typically of the order of 5% to 15% of mixture in 85% to 95% of water, these percentages being by mass relative to the total mass of the water+compound+oil mixture).

The compositions of the invention, and very particularly those comprising polymers of formula (Ia) and (Ib), have the advantage of not foaming very much. In that respect, they are as advantageous as the agents of Lubrhophos® LB400 type and much more advantageous than Lubrhophos® RD510E.

Furthermore, the compounds of the invention, and very particularly the compounds of formula (Ia) and (Ib), have a lower tendency to precipitate by forming soaps in hard water. In addition, they have a very low ecotoxicity, in particular lower than that of Lubrhophos® LB400. Thus, the compositions of the invention constitute a very advantageous alternative to Lubrhophos® LB400.

Various aspects and advantages of the invention will be further illustrated by the examples below.

EXAMPLES

Example 1

Composition Comprising a Polymer of Formula (Ib)
Step 1: Alkoxylation (Propoxylation then Ethoxylation)
The following reactants were used, in the proportions indicated in percentages by mass relative to the total mass of the reactants:
Lauryl alcohol $CH_3-(CH_2)_{11}-OH$: 21.4%
Potassium hydroxide: 0.1%
Propylene oxide: 47.3%
Ethylene oxide: 31.1%
Acetic acid: 0.1%

The lauric acid and the potassium hydroxide were charged to a recirculating reactor equipped with an internal stirrer. They were dehydrated under vacuum at 130° C. for 30 minutes (final moisture <0.030%).

The propylene oxide was then introduced slowly, while cooling (exothermic reaction) in order to maintain the temperature at 130° C.±2° C.

At the end of this propoxylation, the reaction medium was maintained at the temperature of 130° C.±2° C. until a constant pressure was obtained in the reactor, indicating the end of the consumption of the propylene oxide. The ethylene oxide was then introduced slowly, here too while cooling owing to exothermicity in order to maintain the temperature at 130° C.±2° C.

At the end of this ethoxylation, the reaction medium was maintained at the temperature of 130° C.±2° C. until a constant pressure was obtained in the reactor, indicating the end of the consumption of the ethylene oxide.

The medium was then cooled to 50° C. and neutralized by addition of acetic acid.

Step 2: Formation of the Phosphate Ester
The following reactants were used, in the proportions indicated in percentages by mass relative to the total mass of the reactants:
lauryl alcohol alkoxylate formed in step 1: 94.25%
$H_3PO_2$, 50% aqueous solution: 0.2%
$P_2O_5$: 4.85%
Water: 0.5%
Hydrogen peroxide: 0.2%

The lauryl alcohol alkoxylate formed in step 1 was charged at 40° C. to a reactor equipped with a magnetic stirrer and under a nitrogen atmosphere, and the aqueous solution of $H_3PO_2$ was immediately introduced so as to prevent an untimely oxidation at the end of the reaction.

The $P_2O_5$ was added gradually, over a period of 5 hours, while maintaining the temperature at 60° C. After the end of the addition of $P_2O_5$, the reaction was left to continue at 80° C. for two hours.

At the end of these two hours, water was added and the medium was left to cool to 60° C. Once this temperature was reached, the hydrogen peroxide solution was added.

Example 2

Properties of the Polymer Compositions of Example 1
The polymer composition synthesized in the preceding example was used for the preparation of emulsions under the conditions below:

The composition as obtained at the end of example 1 (which is a polymer concentrate) was diluted in deionized water with a concentrate/added water weight ratio of 10/90 in a 100 ml graduated cylinder, while buffering the pH to 9 (MEA solution). The buffered aqueous medium was then mixed with a naphthenic oil (Nytex 810 from the company Nynas), with an aqueous medium/oil weight ratio of 20/80, whereby a first emulsion E1 was formed.

At the same time, a second emulsion E2 was produced under the same conditions, but by replacing the deionized water with hard water comprising 347 mg/l of $CaCO_3$ and 41.1 mg/l of $MgCO_3$.

Emulsifying Properties

The short-term stability (after 30 minutes) and the long-term stability (after 7 days, at 40° C.) the emulsion of the emulsions E1 and E2 was evaluated as follows:

Depending on the stability of an emulsion, several phases may appear in addition to the phase constituting the emulsion: a cream phase and/or an oil phase (generally supernatant) and/or an aqueous phase (generally below the emulsion). The stability may be assessed by measuring the respective volumes of the various phases, and an emulsion stability index $I_{stability}$ is defined as follows:

$I_{stability}$=100 volume of the cream phase (expressed in ml)−5×volume of the oil oil phase (expressed in ml)−5×volume of the aqueous phase (expressed in ml)

The emulsion is all the more stable, the higher its stability index is:

The emulsion is said to be:
"very stable" from 95
"acceptable" between 80 and 95
"not very stable" below 80 and down to 60
"unstable" below 60

The dispersions E1 and E2 are of very stable type, with stability indexes of at least 95, reported in table 1 below:

TABLE 1 short-term and long-term stability of the emulsions

| Emulsion | $I_{stability}$ after 30 minutes | $I_{stability}$ after 7 days at 40° C. |
|---|---|---|
| E1 | 95 | 98 |
| E2 | 96 | 97 |

Formation of Foam and/or Soap

The foaming tendency was evaluated according to a test using a centrifugal pump and a 2 l graduated cylinder with a water jacket equipped with a side outlet close to the bottom of the cylinder. The emulsions were introduced into the cylinder up to the 1000 ml graduation mark, and they were pumped via the outlet at the bottom of the cylinder with a flow rate of 250 l/h, and reinjected via the pump into the cylinder, from a height of 390 mm above the 1000 ml graduation mark. The pumping was carried out with a view to obtaining formation of foam reaching the 2000 ml graduation mark, over a maximum duration $t_{MAX}$ of 5 hours:

In the case where the 2000 ml graduation mark was reached before 5 hours: the time ($t_{2000}$<$t_{MAX}$) taken to reach the 2000 ml graduation mark (namely a foam volume $V_{max}$ corresponding to the volume between the 1000 ml and 2000 ml indices) was noted and the pumping was immediately stopped at $t_{2000}$, then the volume of foam ($V_{t2000+15min}$) above the 1000 ml graduation mark at the time $t_{2000m}$+15 minutes was measured.

In the case where the graduation mark was not reached after 5 hours: the volume of foam ($V_{5h}$<$V_{max}$) achieved above the 1000 ml graduation mark after five hours ($t_{MAX}$) was measured and the pump was stopped after 5 hours, then the volume ($V_{5h+15min}$) of foam above the 1000 ml graduation mark was measured 15 minutes after stopping the pump.

For both cases, the following are defined:
a pumping end time $t_P$
equal to $t_{2000}$ in the first case and to $t_{MAX}$ in the second case
a pumping end volume $V_P$
equal to $V_{MAX}$ in the first case and to $V_{5h}$ in the second case
a volume of foam after resting for 15 minutes $V_R$
equal to $V_{MAX}$ in the first case and to $V_{5h}$ in the second case Two indices reflecting the profile of the foam are calculated as follows:
Initial foam level index $I_M$:

$I_M$=100−10×(1+log($V_P/t_P$))

Defoaming index $I_D$:

$I_D$=100×($V_P$−$V_R$)/$V_P$

The possible formation of soap on the walls was also determined visually.

The results obtained for the dispersions E1 and E2 are reported in table 1 below:

TABLE 2 foaming profiles of the emulsions

| Emulsion | $I_M$ | ID | Soap formation |
|---|---|---|---|
| E1 | 70 | 85 | Very little |
| E2 | 75 | 95 | Very little |

Wear-Resistant Properties

They were evaluated using the ASTM D2670 method.

The tribometer used is a Falex machine equipped with a "Pin and Vee blocks" system, immersed in the emulsions to be tested, at a temperature maintained at 24° C. (in a water-jacketed tank) and at 700 lbs for 10 min.

The wear is determined by the loss of weight of the "Pin and Vee blocks" system, which reflects the degree of wear. A very small loss of weight of the order of 10 mg was obtained for the two emulsions, which reflects very good lubricating properties.

Inhibition of Corrosion (Aluminum)

The emulsions E1 and E2 were tested on three types of aluminum-based alloys, namely the alloys 2024, 6061 and 7075.

Test specimens formed by each of the alloys were submerged in the emulsions in sealed bottles and maintained at 40° C. under these conditions for four weeks.

The corrosion is evaluated visually, the surface turning to dark grey, or even to black, in the case of corrosion ("staining"). No significant corrosion was detected after four weeks, unlike controls in water.

It is also possible to quantify the mass uptake of the samples after 4 weeks, which reflects the corrosion: less than 0.1% by mass with the emulsions E1 and E2 versus around 30% by mass with water.

The invention claimed is:

1. A lubricating formulation, comprising an emulsion and a polymer composition comprising polymers of formula (I) below:

$$[R-O(-CH(CH_3)-CH_2O-)_n(CH_2-CH_2O-)_p-]_{1+x}P(=O)(OH)_{2-x} \quad (I)$$

wherein:
- R is a linear or branched, saturated or unsaturated hydrocarbon-based group comprising from 8 to 12 carbon atoms
- n is a number, integer or not, between 6.5 and 20
- p is a number, integer or not, between 4 and 25
- x is a number between 0 and 1 wherein the emulsion has an emulsion stability index greater than 95.

2. The lubricating formulation as claimed in claim 1, wherein the R group is a saturated or monounsaturated alkyl group.

3. The lubricating formulation as claimed in claim 2, wherein the polymers are polymers of following formula (Ia):

$$[CH_3-(CH_2)_{11}-O-(CH(CH_3)-CH_2O-)_n(-CH_2-CH_2O-)_p]_{1+x}P(=O)(OH)_{2-x} \quad (Ia)$$

wherein n, p and x are as defined.

4. The lubricating formulation as claimed in claim 1, wherein n is between 6.5 and 15.

5. The lubricating formulation as claimed in claim 1, wherein p is between 4.5 and 20.

6. The lubricating formulation as claimed in claim 1, wherein n is equal to 7.5 and p is equal to 5.

7. The lubricating formulation as claimed in claim 6, wherein the polymers are polymers of following formula (Ib):

$$[CH_3-(CH_2)_{11}-O-(CH(CH_3)-CH_2O)_{7.5}(-CH_2-CH_2O-)_5]_{1+x}-P(=O)(OH)_{2-x} \quad (Ib)$$

wherein x is as defined.

8. The lubricating formulation according to claim 1 wherein the formulation is a lubricating formulation for cutting metals.

9. The lubricating formulation according to claim 1 wherein the formulation is a lubricating formulation for working or shaping aluminum.

10. The lubricating formulation according to claim 1, wherein x is a number between 0.1 and 0.9.

11. The lubricating formulation according to claim 2, wherein the R group is a linear, saturated or monounsaturated alkyl group.

12. The lubricating formulation according to claim 4, wherein n is between 7 and 10.

13. The lubricating formulation according to claim 5, wherein p is between 4.5 and 10.

14. The lubricating formulation according to claim 9 wherein the formulation is a lubricating formulation for cutting aluminum.

15. The lubricating formulation according to claim 1, wherein 5% to 30% by mass of the polymer is incorporated in an oil to form a mixture.

16. The lubricating formulation according to claim 15, wherein 5% to 15% of the mixture is mixed with 85% to 95% of water to form an emulsion.

* * * * *